United States Patent [19]
Zhou

[11] Patent Number: 5,864,985
[45] Date of Patent: Feb. 2, 1999

[54] METHOD FOR PRODUCING PHALAENOSIS CLONE PLANTS THROUGH ROOT TIP CULTURE

[75] Inventor: Tian Su Zhou, Nitta-machi, Japan

[73] Assignee: Sapporo Breweries Limited, Tokyo, Japan

[21] Appl. No.: 832,360

[22] Filed: Apr. 2, 1997

[30]     Foreign Application Priority Data

Apr. 3, 1996  [JP]  Japan ..................................... 8-104743

[51] Int. Cl.$^6$ ............................. A01B 79/00; A01G 1/00; A01H 1/04; A01H 1/02
[52] U.S. Cl. .............................. 47/58; 800/200; 800/205; 800/DIG. 62; 800/220; 435/420; 435/430
[58] Field of Search ................................ 47/58; 800/200, 800/205, DIG. 62, 220; 435/420, 430

[56]            References Cited

PUBLICATIONS

Yoneda et al. (1988). Bull. Coll. Agr. & Vet. Med., Nihon Univ., No. 45, pp.: 191–196, 1988.
Michio Tanaka, et al., American Orchid Society, vol. 45, pp. 1022–1024, Nov. 1976, "Plantlet Formation by Root–Tip Culture in Phalaenopsis".
Derwent Abstracts, AN 95–008999, JP6292477, Oct. 21, 1994.
WPI Abstracts, AN 95–009000, JP6292478, Oct. 21, 1994.
G. R. Price, et al., American Orchid Society Bulletin, vol. 53, No. 10, 1984, "Sources of Orchid Protoplasts for Fusion Experiments", (Abstract Only).
Tian–Su Zhou, Plant Cell Reports, vol. 15, 1995, pp. 181–185, "In Vitro Culture of Doritaenopsis: Comparison Between Formation of the Hyperhydric Protocorm–Like Body (PLB) and the Normal PLB".
T. W. Yam, et al., Lindleyana, vol. 6, No. 3, pp. 151–153, 1991, "Root–Tip Culture of Several Native Orchids of Hong Kong".
Derwent Abstracts, AN 97–252898, JP9084477, Mar. 31, 1997.
M. Kobayashi, et al., Tochigi Pref. Agr. Exp. Stn., pp. 664–665, Feb. 1990, "Studies on the Vegetative Propagation of Phalaenopsis Through Root–Tip Culture" (With English Translation).

*Primary Examiner*—Hobert A. Wax
*Assistant Examiner*—Tekchand Saidha
*Attorney, Agent, or Firm*—Oblon, Spivak, McClelland, Maier & Neustadt, P.C.

[57]            ABSTRACT

Disclosed is a method for producing *Phalaenopsis orchid* clone plants, which comprises cutting the tip of a growing root of a *Phalaenopsis orchid* that has been prepared under sterile conditions at a length of from 1 to 5 mm to prepare a root tip for culture having said predetermined length, cultivating said root tip in a PLB-inducing medium under sterile conditions to thereby induce PLB therein, further cultivating said PLB in a propagating medium, and then re-differentiating said PLB in a re-differentiation medium. The method is practicable and stably given PLB of *Phalaenopsis orchids*.

17 Claims, 1 Drawing Sheet

METHOD FOR PRODUCING PHALAENOSIS CLONE PLANTS THROUGH ROOT TIP CULTURE

FIELD OF THE INVENTION

The present invention relates to a method for producing Phalaenopsis clone plants through root tip culture, and more precisely, to a method for stably mass-producing Phalaenopsis clone plants through root tip culture.

BACKGROUND OF THE INVENTION

Phalaenopsis attract a great deal of public attention. For cultivation of plants, recently, mass-production of plants through clonal propagation is being in full flood. To the induction of protocorm-like bodies (PLB) that are in the initial stage for the production of clonal plants, at present, applied are conventional leaf segment culture and also other spike-axillary bud culture and root tip culture (M. Tanaka, 1987, Studies on the Clonal Propagation of Phalaenopsis through in-vitro Culture, Memoirs of Faculty of Agriculture, Kagawa University, No. 49; 1–85; S. Ichihashi, 1992, Micropropagation of Phalaenopsis through the Culture of Lateral Buds from Young Flower Stalks, Lindleyana, 7(4): 208–215; M. Kobayashi, M. Komatsuda & S. Yoneuchi, 1990, Studies on the vegetative propagation of Phalaenopsis through root tip culture, J. J. Soc. Hort. Sci., 63(suppl.2); 664–671).

However, in the process of the induction of PLB through such known root tip culture (M. Kobayashi, M. Komatsuda & S. Yoneuchi, 1990, Studies on the vegetative propagation of Phalaenopsis through root tip culture, J. J. Soc. Hort. Sci., 63(suppl.2); 664–671) or any other culture, the degree of the intended induction is often low or, as the case may be, no induction is attained for some varieties, hybrids and materials.

Because of such unsure induction of PLB, mass-production of plants through clonal propagation could not apply to some varieties and hybrids of Phalaenopsis. Therefore, in order to improve the efficiency in the induction of PLB, it is necessary to establish an effective method of initial culture capable of overcoming the difference in varieties and hybrids and the difference in materials.

The reasons for such unsure induction of PLB in known root tip culture are believed to be essentially that the surface of the meristematic tissue of a root tip, which is a material of a PLB-forming source, will be often damaged while being sterilized, and that said tissue could not satisfactorily display its ability for cell division due to conditions and methods unsuitable for cultivating it thereby resulting in that its ability to form PLB is lowered.

SUMMARY OF THE INVENTION

The object of the present invention is to solve the above-mentioned problems and to provide a practicable and stable method for inducing PLB of *Phalaenopsis orchids* through root tip culture.

The present inventor has assiduously studied root tip culture of *Phalaenopsis orchids* and, as a result, has found that, when a root tip as cut out of the tip of a root to have a predetermined length is used, PLB can be formed to an elevated degree. After further studies on the method for processing said root tip, the media for PLB induction from said root tip and also the conditions for pre-culture of said root tip, the inventor has at last developed a practicable method for induction of PLB of *Phalaenopsis orchids*, and has completed the present invention.

Specifically, the present invention is a method for producing *Phalaenopsis orchid* clone plants, which comprises cutting the tip of a growing root of a *Phalaenopsis orchid* that has been prepared under sterile conditions at a length of from 1 to 5 mm to prepare a root tip for culture having said predetermined length, cultivating said root tip In a PLB-inducing medium under sterile conditions to thereby induce PLB therein, further cultivating said PLB in a propagating medium, and then re-differentiating said PLB in a re-differentiation medium.

DETAILED DESCRIPTION OF THE PREFERRED EMBODIMENTS

Now, the present invention is described in detail hereinunder.

Varieties and hybrids of *Phalaenopsis orchid* for use in the present invention are not specifically defined. For example, employable herein are *Phalaenopsis orchids* of the genus Doritaenopsis, such as Dtps. Odoriko, Dtps. Zuma Headliner, and Dtps. White Wondern; and those of the genus Phalaenopsis, such as Phal. Orchid World, Phal. Zuma's Pixie, and Phal. Alfenso Morenon.

In the present invention, any of the above-mentioned hybrids and even any other different varieties and hybrids of *Phalaenopsis orchid* can be used to effectively induce PLB.

The growing root of a *Phalaenopsis orchid* as referred to herein, which is prepared under sterile conditions, may include, for example, growing roots of plants which are cultivated under ordinary sterile conditions, those of spike-axillary bud-derived plants which are cultivated under ordinary sterile conditions, and those of plants growing in greenhouses. The growing roots of plants as cultivated under sterile conditions are preferred to those of plants as grown in greenhouses, as they can be directly used herein without being subjected to sterilization of their surfaces and, therefore, they are not damaged with such surface sterilization. For the growing roots of plants as grown in greenhouses, they shall be used after having been subjected to sterilization of their surfaces according to known methods (for example, see M. Kobayashi, M. Komatsuda & S. Yoneuchi, 1990, Studies on the vegetative propagation of Phalaenopsis through root tip culture, J. J. Soc. Hort. Sci., 63(suppl.2); 664–665).

The root of a *Phalaenopsis orchid* thus prepared is cut at a length of from 1 to 5 mm, preferably from 2 to 4 mm, from its tip, using a sterile knife to give a root tip for culture. If the length of the root tip is smaller than the lowermost limit, many such root tips will die, resulting in the decrease in the survival rate of root tip. On the other hand, if too long root tips are used, the degree of PLB formation will be low though their survival rate will be high.

Figure 1A:
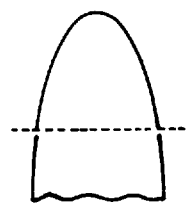
FIG. 1 shows one embodiment of preparing a root tip of a *Phalaenopsis orchid* to be subjected to root tip culture according to the present invention, in which 1A indicates the way of cutting a root, 1B is a root tip obtained, and 1C is a notched root tip.
Figure 1B:
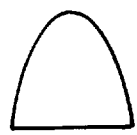
Figure 1C:

The degree of PLB formation will be elevated effectively, if the top of the root tip for culture is notched to a depth of from 0.5 to 2.0 mm, preferably to a depth of about ½ of the length of said root tip, depending on the length thereof (see FIG. 1).

Next, the thus-processed root tip for culture is placed on a PLB-inducing medium with its cut surface being kept in contact with the medium.

As the PLB-inducing medium, usable are any ordinary media for plant tissue culture. For example, used herein is MS medium or ⅓ MS medium. Preferably, the PLB-inducing medium may contain any saccharide of, for example, polysaccharides, monosaccharides and sugar alcohols (e.g., sucrose, sorbitol). For sucrose, its content in the medium may be from 0.5 to 3%, preferably 0.5%. For sorbitol, its content therein may be from 0.05 to 0.5%, preferably 0.1%. The addition of sorbitol to the medium may increase the degree of PLB induction and also the survival rate of root tip being cultivated.

Moreover, the addition of plant hormones to the PLB-inducing medium is more advantageous. For plant hormones, auxins such as naphthalene-acetic acid (NAA) may be added to the medium in an amount of from 0.005 to 0.05 ppm, preferably 0.01 ppm; or cytokinins such as benzyladenine (BA) may be added thereto in an amount of from 1 to 15 ppm, preferably 5 ppm.

In the method of the present invention, in general, a gelling agent such as Gellan gum or agar may be used as the support for the medium. For Gellan gum, it may be added to the medium in an amount of from 0.2 to 0.4%, preferably from 0.25 to 0.3%.

The induction culture for PLB may be conducted in any ordinary manner. In general, for example, root tips are cultivated at from 20° to 28° C. preferably at 25° C. for from 30 to 60 days, while being exposed to light (at an illuminance of from 500 to 5000 lux, preferably 3000 lux) continuously or for 16 hours a day.

To induce PLB, low-temperature culture is preferred in the initial stage of cultivating root tips. For example, prior to being cultivated under the above-mentioned ordinary conditions, root tips are preferably pre-cultivated at low temperatures of from 5° to 15° C., preferably at 10° C. for from 8 to 72 hours, preferably for about 12 hours, while being exposed to light under the same conditions as for such ordinary culture, to produce better results.

As a result of said induction culture of root tip for PLB, PLB are formed. The ability of root tips to form PLB varies, depending on the varieties and hybrids of *Phalaenopsis orchid* from which said root tips are derived. Therefore, the cultivation of root tips shall be continued for an appropriate period of time.

Next, to regenerate the plants of a *Phalaenopsis orchid* from PLB thus induced from the root tip of the *Phalaenopsis orchid* through the culture of said root tip, PLB may be transplanted into ordinary sterile media, in which PLB may grow with ease to give the intended plants. In general, one PLB grows to give one plants. Therefore, in order to mass-produce a large number of the intended plants, PLB must be propagated. For this, in order to facilitate the re-differentiation of PLB into plants, the culture environment for the propagation of PLB, which includes, for example, the degree of lighting and that of aeration, must be kept all the time constant.

In the present invention, PLB as induced from root tip of a *Phalaenopsis orchid* are cultivated in a propagation medium, and thereafter said PLB are re-differentiated in a re-differentiation medium to obtain plants of said *Phalaenopsis orchid*.

The PLB propagation medium for use in the present invention may be any ordinary medium that is generally used for ordinary propagation of PLB. Concretely, it may include, for example, MS media. Preferred are Tanaka's V & W-modified media (M. Tanaka, 1987, Studies on the Clonal Propagation of Phalaenopsis through in-vitro Culture, Memoirs of Faculty of Agriculture, Kagawa University, No. 49; 1–85). Regarding the conditions for propagating PLB, PLB may be cultivated and propagated at from 20° to 28° C., preferably from 23° to 26° C., while being exposed to light at an illuminance of from 200 to 10000 lux, preferably 2000 lux, for from 8 to 24 hours a day, preferably for 16 hours a day.

The re-differentiation medium for use in the present invention may be any ordinary one that is generally used for ordinary re-differentiation of PLB. Concretely, it may include, for example, MS media. Preferred embodiments of the media are the present inventor's V & W-modified media (T. S. Zhou, 1995, in-vitro Culture of Doritaenopsis: Comparison Between Formation of Hyperhydric Protocorm-like-body (PLB) and the Normal PLB., Plant Cell Reports, 15: 181–185). The conditions for the intended re-differentiation may be the same as those mentioned hereinabove.

Now, the present invention is described in detail by means of the following Examples, which, however, are not intended to restrict the scope of the invention.

EXAMPLE 1

Growing roots derived from plants of Dtps. Odoriko as cultivated according to spike-axillary bud culture were used herein as samples. For the preparation and cultivation of the spike-axillary buds of Dtps. Odoriko, referred to was a Tanaka method (M. Tanaka, 1987, Studies on the Clonal Propagation of Phalaenopsis through in-vitro Culture, Memoirs of Faculty of Agriculture, Kagawa University, No. 49: 1–85).

The roots were cut at a length of 1 mm, 2 mm and 5 mm from their tips to prepare root tips to be cultivated herein. Apart from these, also prepared herein other root tips of 2 mm long, which were notched at their tops to have a notch of about 1.0 mm in depth. 0.5% of sucrose and 0.4% of Gellan gum were added to a ⅓ MS medium to prepare a medium for cultivation of the root tips. The root tips were put on this medium and cultivated at 25° C., while being exposed to light at 3000 lux for 16 hours a day. After 2 months, the root tips were checked. The results obtained herein are shown in Table 1 below.

TABLE 1

| Length of Root Tips | Number of Root Tips | Number of PLB Formed | Percentage of PLB Formation | Number of Living Root Tips | Survival Rate (%) |
| --- | --- | --- | --- | --- | --- |
| 1 min | 20 | 4 | 20% | 4 | 20 |
| 2 min | 20 | 5 | 25 | 10 | 50 |
| 5 min | 20 | 3 | 15 | 17 | 85 |
| Notched | 20 | 7 | 35 | 10 | 50 |

As in Table 1 above, the survival rate in the group of root tips of 2 mm long was about 50%, and the percentage of PLB formation was increased in said group. In particular, the percentage of PLB formation was significantly increased in the group of notched root tips.

EXAMPLE 2

Growing roots derived from plants of Dtps. Odoriko as cultivated according to spike-axillary bud culture were used herein as samples. The spike-axillary buds of Dtps. Odoriko were prepared and cultivated in the same manner as in Example 1.

The roots were cut at a length of 2 mm from their tips to prepare root tips to be cultivated herein, which were notched at their tops to have a notch of about 1.0 mm in depth.

Three media were prepared herein for cultivation of the root tips. The first is a medium a, which was prepared by adding 0.5% of sucrose and 0.4% of Gellan gum to a ⅓ MS medium; the second is a medium b, which was prepared by adding 0.5% of sucrose, 0.1% of sorbitol and 0.4% of Gellan gum to a ⅓ MS medium; and the third is a medium c, which was prepared by adding 0.5% of sucrose, 0.1% of sorbitol, 0.01 ppm of NAA, 5 ppm of BA and 0.4% of Gellan gum to a ⅓ MS medium. The root tips were put on any of these media and cultivated at 25° C., while being exposed to light at 3000 lux for 16 hours a day. After 2 months, the root tips were checked. The results obtained herein are shown in Table 2 below.

TABLE 2

| Medium | Number of Root Tips | Number of PLB Formed | Percentage of PLB Formation | Number of Living Root Tips | Survival Rate (%) |
|---|---|---|---|---|---|
| a | 40 | 12 | 30% | 18 | 45 |
| b | 40 | 17 | 43 | 20 | 50 |
| c | 40 | 26 | 65 | 33 | 83 |

As in Table 2 above, the addition of plant hormones such as NAA and BA to the medium along with sorbitol resulted in the noticeable increase in the survival rate and the percentage of PLB formation.

EXAMPLE 3

Growing roots derived from plants of Dtps. Odoriko as cultivated according to spike-axillary bud culture were used herein as samples. The spike-axillary buds of Dtps. Odoriko were prepared and cultivated in the same manner as in Example 1.

The roots were cut at a length of 2 mm from their tips to prepare root tips to be cultivated herein, which were notched at their tops to have a notch of about 1.0 mm in depth.

0.5% of sucrose, 0.1% of sorbitol, 0.01 ppm of NAA, 5 ppm of BA and 0.4% of Gellan gum were added to a ⅓ MS medium to prepare a medium for cultivation of the root tips. The root tips were put on this medium and pre-cultivated under various conditions (at from 5° to 15° C. for from 12 to 72 hours), while being exposed to light at 3000 lux, and thereafter further cultivated at 25° C. in an ordinary manner, while being exposed to light at 3000 lux for 16 hours a day. After 2 months, the root tips were checked. The results obtained herein are shown in Table 3 below. The samples in the control group were not pre-cultivated but were directly cultivated at 25° C. with exposure to light at 3000 lux for 16 hours a day, and checked after 2 months.

TABLE 3

| Temperature in Pre-cultivation (°C.) | Time for Pre-cultivation (hr) | Number of Root Tips | Number of PLB Formed | Percentage of PLB Formation | Number of Living Root Tips | Survival Rate (%) |
|---|---|---|---|---|---|---|
| 5 | 12 | 10 | 4 | 40% | 6 | 60 |
|  | 24 | 10 | 1 | 10 | 5 | 50 |
|  | 72 | 10 | 0 | 0 | 1 | 10 |
| 10 | 12 | 10 | 7 | 70% | 8 | 80 |
|  | 24 | 10 | 6 | 60 | 8 | 80 |
|  | 72 | 10 | 1 | 10 | 4 | 40 |
| 15 | 12 | 10 | 5 | 50% | 7 | 70 |
|  | 24 | 10 | 5 | 20 | 8 | 80 |
|  | 72 | 10 | 2 | 20 | 8 | 80 |
| Control | — | 10 | 6 | 60 | 7 | 70 |

As in Table 3 above, the root tips of the group that had been pre-cultivated at a low temperature of 10° C. for 12 hours gave an increased percentage of PLB formation and an increased survival rate, as compared with those of the other groups.

As has been described in detail hereinabove with reference to its preferred embodiments, the present invention increases the percentage of the formation of PLB of *Phalaenopsis orchids* and also the survival rate of root tips of *Phalaenopsis orchids*, while increasing the degree of regeneration of plants of *Phalaenopsis orchids*. Thus, it is expected that the present invention contributes to a high degree to overcoming the problems to be caused by the difference in the varieties and hybrids of *Phalaenopsis orchids* in the production of clonal plants of *Phalaenopsis orchids*.

The entire disclosure of Japanese Patent Application No. 8-104743 filed on Apr. 3, 1996 including specification, claims and summary are incorporated herein by reference in its entirety.

What is claimed is:

1. A method for producing *Phalaenopsis orchid* clone plants, which comprises cutting a tip of a growing root of a *Phalaenopsis orchid* that has been prepared under sterile conditions at a length of from 1 to 5 mm, notched at its tip, to prepare a root tip for culture having said predetermined length, cultivating said root tip in a PLB-inducing medium under sterile conditions to thereby induce PLB therein, further cultivating said PLB in a propagating medium, and then re-differentiating said PLB in a re-differentiation medium.

2. The method as claimed in claim 1, wherein the PLB-inducing medium contains sorbitol, or sorbitol and plant hormones.

3. The method as claimed in claim 1, wherein the root tip is pre-cultivated at a low temperature in the initial stage of inducing PLB therefrom.

4. The method as claimed in claim 1, wherein the *Phalaenopsis orchid* is a *Phalaenopsis orchid* of a genus Doritaenopsis or a genus Phalaenopsis.

5. The method of claim 1, wherein said length is from 2 to 4 mm.

6. The method of claim 1, wherein said PLB-inducing medium comprises at least one member selected from the group consisting of auxins and cytokinins.

7. The method of claim 1, wherein said PLB-inducing medium comprises NAA and BA.

8. The method of claim 3, wherein said low temperature is 10°–15° C.

9. A method for cloning Phalaenopsis, comprising:

cultivating a cut root tip 1–5 mm in length and notched to form a PLB.

10. The method of claim 9, wherein said cultivating is in a medium comprising sorbitol, or sorbitol and at least one plant hormone.

11. The method of claim 9, further comprising:

cultivating said PLB; and re-differentiating said PLB.

12. The method of claim 9, wherein said Phalaenopsis is a plant selected from the group consisting of genus Doritaenopsis and genus Phalaenopsis.

13. The method of claim 9, wherein said cut tip has a length of 2–4 mm.

14. The method of claim 9, wherein said cultivating is in a medium comprising at least one member selected from the group consisting of auxins and cytokinins.

15. The method of claim 9, wherein said cultivating is in a medium comprising NAA and BA.

16. The method of claim 9, further comprising pre-cultivating said cut tip at a temperature of 10°–15° C.

17. In a method of cloning a *Phalaenopsis orchid,* the induction of PLB by cultivating a cut root tip, propagating the PLB and re-differentiating the PLB, the improvement comprising cultivating a cut root tip having a length of 1–5 mm, wherein said root tip is notched.

* * * * *

UNITED STATES PATENT AND TRADEMARK OFFICE
CERTIFICATE OF CORRECTION

PATENT NO.   : 5,864,985
DATED        : February 2, 1999
INVENTOR(S)  : Tian Su ZHOU It is certified that error appears in the above-identified patent and that said Letters Patent is hereby corrected as shown below:

On the title page, item [54] and Column1, line 1:

The word Phalaenosis is --PHALAENOPSIS--

Signed and Sealed this

Seventeenth Day of August, 1999

Attest:

Attesting Officer

Q. TODD DICKINSON

Acting Commissioner of Patents and Trademarks